(12) United States Patent
Newton et al.

(10) Patent No.: US 8,273,878 B2
(45) Date of Patent: Sep. 25, 2012

(54) PROCESS FOR THE PREPARATION OF PYRIMIDINE COMPOUNDS

(75) Inventors: Lee Newton, Grangemouth (GB); Mark Bailey, Grangemouth (GB)

(73) Assignee: AstraZeneca UK Limited, London (GB)

( * ) Notice: Subject to any disclaimer, the term of this patent is extended or adjusted under 35 U.S.C. 154(b) by 519 days.

(21) Appl. No.: 12/404,575

(22) Filed: Mar. 16, 2009

(65) Prior Publication Data

US 2009/0264654 A1 Oct. 22, 2009

Related U.S. Application Data

(62) Division of application No. 10/537,723, filed as application No. PCT/GB03/05359 on Dec. 9, 2003, now Pat. No. 7,524,955.

(30) Foreign Application Priority Data

Dec. 16, 2002 (GB) ................................. 0229243.1
Feb. 17, 2003 (GB) ................................. 0303589.6
Aug. 7, 2003 (GB) ................................. 0318515.4

(51) Int. Cl.
C07D 239/02 (2006.01)
(52) U.S. Cl. ...................................................... 544/297
(58) Field of Classification Search ................ 544/297
See application file for complete search history.

(56) References Cited

U.S. PATENT DOCUMENTS

| | | | |
|---|---|---|---|
| 4,689,414 A * | 8/1987 | Atwal | ................................ 544/297 |
| 4,698,340 A | 10/1987 | Takaya et al. | |
| 5,500,424 A | 3/1996 | Nagamine et al. | |
| 5,593,992 A | 1/1997 | Adams et al. | |
| 5,681,957 A | 10/1997 | Wolters et al. | |
| 5,958,934 A | 9/1999 | Berger et al. | |
| 6,057,332 A | 5/2000 | Michne et al. | |
| 6,278,001 B1 | 8/2001 | Solladie et al. | |
| 6,579,984 B1 | 6/2003 | Veith et al. | |
| 6,784,171 B2 | 8/2004 | Taylor et al. | |
| 6,844,437 B1 | 1/2005 | Taylor et al. | |
| 6,855,716 B2 | 2/2005 | Ohno et al. | |
| 6,870,059 B2 | 3/2005 | Kooistra et al. | |

FOREIGN PATENT DOCUMENTS

| | | |
|---|---|---|
| EP | 0521471 | 10/2000 |
| JP | 06-256318 | 9/1994 |
| JP | 06256318 | 9/1994 |
| WO | WO 90/03973 | 4/1990 |
| WO | WO 92/01675 | 2/1992 |
| WO | WO 93/08823 | 5/1993 |
| WO | WO 96/14846 | 5/1996 |
| WO | WO 97/19917 | 6/1997 |
| WO | WO 97/21687 | 6/1997 |
| WO | WO 99/07695 | 2/1999 |
| WO | WO 00/49014 | 8/2000 |
| WO | WO 00/78730 | 12/2000 |
| WO | WO 01/04100 | 1/2001 |
| WO | WO 01/60804 | 8/2001 |
| WO | WO 01/72706 | 10/2001 |
| WO | WO 01/85702 | 11/2001 |
| WO | WO 01/85975 | 11/2001 |
| WO | WO 02/06266 | 1/2002 |
| WO | WO 03/006439 | 1/2003 |
| WO | WO 03/059901 | 7/2003 |
| WO | WO 03/087112 | 10/2003 |
| WO | WO 03/106447 | 12/2003 |
| WO | WO 2004/014872 | 2/2004 |
| WO | WO 2004/054986 | 7/2004 |
| WO | WO 2004/103977 | 12/2004 |
| WO | WO 2004/108691 | 12/2004 |
| WO | WO 2005/023779 | 3/2005 |
| WO | WO 2005/028450 | 3/2005 |
| WO | WO 2005/042522 | 5/2005 |
| WO | WO 2005/063728 | 7/2005 |
| WO | WO 2006/067456 | 6/2006 |

OTHER PUBLICATIONS

RN 359450-51-4 Registry ED Entered STN: Sep. 28, 2001 CN 5-Pyrimidinecarboxylic acid, 2-amino-1,4-dihydro-4-(4-hydroxy-3-methoxyphenyl)-6-methyl-, ethyl ester (CA Index Name).*

(Continued)

*Primary Examiner* — Erich A Leeser

(74) *Attorney, Agent, or Firm* — Morgan, Lewis & Bockius LLP

(57) ABSTRACT

A process for the preparation of a compound of Formula (1) and intermediates useful therein are provided. The process comprises reacting a compound of formula $R^1$—CO—$CH_2$-E with a compound of formula $R^2$—$CHX^1X^2$ in the presence of a compound of formula $R^3R^4N$—C(=NH)$NH_2$ and a catalyst, thereby to form a dihydropyrimidine; and oxidizing the dihydropyrimidine to form the compound of Formula (I). $R^1$ is H or an alkyl group; $R^2$ is H, an alkyl or aryl group; $R^3$ and $R^4$ are each independently H, alkyl or aryl, or $R^3$ and $R^4$ are linked to form, together with the nitrogen to which they are attached to form a 5 to 7 membered heterocyclic ring; E is H, an unsubstituted alkyl group, an aryl group or an electron withdrawing group; and $X^1$ and $X^2$ are each independently leaving groups, or $X^1$ and $X^2$ together represent =O.

(1)

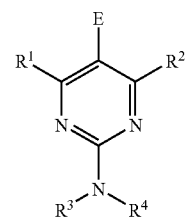

8 Claims, No Drawings

OTHER PUBLICATIONS

RN 359450-51-4 dated Sep. 28, 2001; no author, publisher, edition or volume, or pertinent pages.*

Breaux et al. "An Improved General Synthesis of 4-Aryl-5-Pyrimidinecarboxylates" J. Heterocyclic Chem. 18: 183 (1981).

De Luca et al. "Cellulose Beads: a New Versatile Solid Support for Microwave- Assisted Synthesis. Preparation of Pyrazole and Isoxazole Libraries" J. Comb. Chem. 5(4):465-471 (2003).

Grohe et al. "Synthese und Reaktionen von 2,4-Dichlorpyrimidin-5-carbon-saureestem" Liebigs Ann. Chem. 1025-1035 (1973).

Hannah et al. "Structural studies on bioactive compounds. Part 29: palladium catalysed arylations and alkynylations of sterically hindered immunomodulatory 2-amino-5-halo-4,6-(disubstituted)pyrimidines" Bioorg Med Chem. 8(4):739-750 (2000).

Hauser et al. "Synthesis of 5-phenyl-4,6-dimethyl-2-pyrimidol and derivatives from the cyclization of urea with 3-phenyl-2,4-pentanedione" Journal of Organic Chemistry 18(5): 588-593 (1953).

Kaneko et al. "Preparation of optically active 5,6-epoxyhexanoic acid esters as materials for physiologically active substances" Chemical Abstracts + Indexes, American Chemical Society, Columbus, US 118(11):832 (1993).

Ma et al. "Lanthanide triflate catalyzed Biginelli reaction. One pot synthesis of dihydropyrimidinones under solvent-free condition" J. Org. Chem. 65:3864-3868 (2000).

Menges et al. "Oxidative Degradation of γ-Butyrolactons into 1,3-Diols via a Criegee Rearrangement of Peroxosulfonates. An Enantioselective Synthesis of Compactin Lactone and its Diastereomer" Synlett 12:901-905 (1993).

Presentation given at the 20th International Congress of Heterocyclic Chemistry in Palermo, Aug. 1-5, 2005.

Presentation given at the Gordon Conference on Heterocyclic Compounds, Salve Regina University, Newport, Rhode Island, Jul. 4-9, 2004.

Sakaki et al. "Lipase-catalyzed asymmetric synthesis of 6-(3-chloro-2-hydroxypropyl)-1,3-dioxin-4-ones and their conversion to chiral 5,6-epoxyhexanoates" Tetrahedron: Asymmetry 2(5):343-346 (1991).

Shao et al. "Asymmetric hydrogenation of 3,5-Dioxoesters catalyzed by Ru-binap complex: A short step asymmetric synthesis of 6-substituted 5,6-dihydro-2-pyrones" Tetrahedron 49(10):1997-2010 (1993).

Vanden Eynde et al. "Microwave-mediated Regioselective Synthesis of. Novel Pyrimido[1,2-a]pyrimidines under Solvent-free Conditions" Tetrahedron 57(9):1785-1791 (2001).

Watanabe et al. "Synthesis and Biological Activity of Methanesulfonamide Pyrimidine- and N-Methanesulfonly Pyrrole-Substituted 3,5-Dihydroxy-6-heptenoates, a Novel Series of HMG-CoA Reductase Inhibitors" Bioord. Med. Chem. 5(2):437-444 (1997).

Kappe "Highly versatile solid phase synthesis of biofunctional 4-aryl-3,4-dihydropyrimidines using resin-bound isothiourea building blocks and multidirectional resin cleavage" Bioorganic & Medicinal Chemistry Letters 10(1):49-51 (2000).

* cited by examiner

PROCESS FOR THE PREPARATION OF PYRIMIDINE COMPOUNDS

This application is a Divisional application of U.S. patent application Ser. No. 10/537,723, filed Jun. 7, 2005 now U.S. Pat. No. 7,524,955, which is a U.S. National Phase Application of International Application No. PCT/GB2003/005359, filed Dec. 9, 2003, which claims the benefit of Great Britain Patent Application No. 0229243.1, filed Dec. 16, 2002, Great Britain Patent Application No. 0303589.6, filed Feb. 17, 2003, and Great Britain Patent Application No. 0318515.4, filed Aug. 7, 2003, all of which are hereby incorporated by reference in their entirety.

The present invention concerns a process for the preparation of pyrimidines and intermediate compounds useful in the preparation thereof.

Substituted pyrimidine compounds are valuable compounds for use in particularly the pharmaceutical industry. Certain 2-aminopyrimidine compounds are intermediates used in the preparation of pharmaceutical compounds useful in the treatment of, inter alia, hypercholesterolemia, hyperlipoproteinemia and artherosclerosis. Synthetic routes to substituted pyrimidine compounds have been disclosed in EP-A-0 521 471 and WO01/04100. Nevertheless, it remains desirable to identify alternative routes for the preparation of substituted pyrimidine compounds.

According to a first aspect of the present invention, there is provided a process for the preparation of a compound of Formula (1):

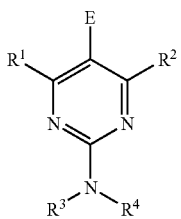

Formula (1)

which comprises a) reacting a compound of formula $R^1$—CO—$CH_2$-E with a compound of formula $R^2$—$CHX^1X^2$ in the presence of a compound of formula $R^3R^4N$—C(=NH)$NH_2$ and a catalyst, thereby to form a dihydropyrimidine; and b) oxidising the dihydropyrimidine produced in step a) to form the compound of Formula (1) wherein $R^1$ is H or an alkyl group;

$R^2$ is H or an alkyl or aryl group;

$R^3$ and $R^4$ are each independently H, alkyl or aryl, or $R^3$ and $R^4$ are linked to form, together with the nitrogen to which they are attached, a 5 to 7 membered heterocyclic ring;

E is H, an unsubstituted alkyl group, an aryl group or an electron withdrawing group; and $X^1$ and $X^2$ are each independently leaving groups, or $X^1$ and $X^2$ together represent =O.

Dihydropyrimidines formed in step a) can be represented by the Formula (2):

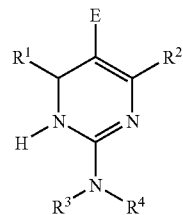

Formula (2)

It will be recognised that the compounds of Formula (2) can exist in a number of tautomeric forms in which the double bonds are delocalised into other positions in the molecule, notably into different positions around the pyrimidine ring. Without wishing to be bound by any theory, it is believed that for certain compounds of Formula 2, the predominant tautomeric form is of Formula (2a):

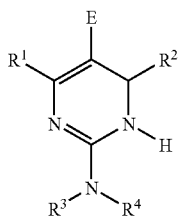

Formula (2a)

Alkyl groups which may be represented by $R^1$ include linear, branched and cyclic alkyl groups commonly comprising from 1 to 8 carbon atoms. Preferred cyclic alkyl groups include cyclopropyl, cyclobutyl, cyclopentyl and cyclohexyl groups. Preferred linear and branched alkyl groups include methyl, ethyl, n-propyl, isopropyl, n-butyl, sec-butyl and tert-butyl groups. Most preferably, $R^1$ represents isopropyl.

Alkyl groups which may be represented by $R^2$ are as described above for $R^1$.

Aryl groups which may be represented by $R^2$ include both homoaryl and heteroaryl groups, and commonly comprise at least one 5 to 7 membered aromatic ring. Examples of aryl groups include phenyl, naphthyl and pyridyl groups. Most preferably, $R^2$ represents a phenyl group.

Alkyl and aryl groups which may be represented by $R^3$ and $R^4$ are as described above for $R^1$ and $R^2$. In certain preferred embodiments, $R^3$ represents methyl and $R^4$ represents H. In other preferred embodiments, both of $R^3$ and $R^4$ are H.

Alkyl and aryl groups which may be represented by $R^1$, $R^2$, $R^3$ and $R^4$ may be unsubstituted or substituted by one or more substituents. Examples of substituents include optionally substituted alkoxy (preferably $C_{1-4}$-alkoxy), optionally substituted alkyl (preferably $C_{1-4}$-alkyl), optionally substituted aryl (preferably phenyl), optionally substituted aryloxy (preferably phenoxy), optionally substituted heterocyclyl, polyalkylene oxide (preferably polyethylene oxide or polypropylene oxide), carboxy, oxo, phosphato, sulpho, nitro, cyano, halo, especially chloro and fluoro, ureido, —$SO_2F$, hydroxy, ester, —$NR^aR^b$, —$COR^a$, —$CONR^aR^b$, —$NHCOR^3$, carboxyester, sulphone, and —$SO_2NR^aR^b$ wherein $R^a$ and $R^b$ are each independently H, optionally substituted alkyl (especially $C_{1-4}$-alkyl) or optionally substituted aryl (preferably phenyl), or, in the case of —$NR^aR^b$, —$CONR^aR^b$ and —SO$_2$NR$^a$R$^b$, R$^a$ and R$^b$ together with the nitrogen atom to which they are attached may represent an aliphatic or aromatic ring system. Optional substituents for any of the substituents described may be selected from the same list of substituents.

Unsubstituted alkyl groups which may be represented by E are those unsubstituted alkyl groups as described above for R$^1$.

Aryl groups which may be represented by E are as described above for R$^2$.

Electron withdrawing groups which may be represented by E include nitro groups; nitrile groups; perhaloalkyl groups, such as trifluoromethyl and pentafluoroethyl; ester groups, especially alkyl carboxylate groups; sulphonamide groups; keto groups; amide groups; and aldehyde groups, especially formyl groups.

E may also represent a group of formula —CHX$^a$X$^b$, wherein X$^a$ and X$^b$ each independently represents a halo, especially a chloro or bromo group, an alkoxy group, especially a C$_{1-4}$alkoxy, such as a methoxy or ethoxy group, an alkylthio group, especially a C$_{1-4}$alkylthio group, or X$^a$ and X$^b$ are linked to form a cyclic acetal or thioacetal commonly comprising, with the carbon to which X$^a$ and X$^b$ are bonded, from 5 to 7 atoms in the ring. When E represents a group of formula —CHX$^a$X$^b$, it is preferred that X$^a$ is the same as X$^b$.

Further groups which may be represented by E are groups of formula —CH$_2$E$^2$, wherein E$^2$ represents halo, especially bromo or chloro, or a phosphorus-containing moiety, such as a phosphate ester, for example of formula —OP(=O)(OR$^c$)$_2$, a phosphonate ester, for example of formula —P(=O)(OR$^c$)$_2$, a phosphite, for example of formula —P(OR$^c$)$_2$, a phosphine, for example of formula —P(R$^c$)$_2$, or a phosphine oxide, for example of formula —P(=O)(R$^c$)$_2$, in each of which R$^c$ represents an alkyl, such as a C$_{1-4}$ alkyl, or an aryl, such as a phenyl, group. When E$^2$ represents a phosphorus-containing moiety, it is preferably a phosphine oxide of formula —P(=O)(R$^d$)$_2$ wherein R$^d$ represents methyl, ethyl or phenyl.

E may also represent a group of formula —CR$^x$=CR$^y$R$^z$, wherein R$^x$, R$^y$ and R$^z$ each independently represent H, alkyl or aryl. Preferably, R$^x$ and R$^y$ represent H, and R$^z$ represents an optionally substituted C$_{1-5}$ alkyl chain. R$^z$ is preferably substituted by two hydroxy groups, commonly present as a protected 1,3-dihydroxy moiety. R$^z$ preferably comprises a terminal carboxyl group, especially a carboxy ester group. R$^z$ is most preferably a group of formula:

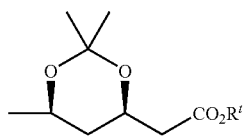

wherein R$^t$ is an alkyl group, preferably a tert-butyl group.

A particular compound of formula R$^1$—CO—CH$_2$-E is of formula:

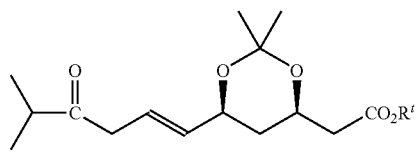

wherein R$^t$ is an alkyl group, preferably a tert-butyl group.

Preferably, E represents a group of formula —CO$_2$(C$_{1-4}$ alkyl), and especially —CO$_2$Me, —CO$_2$Et or —CO$_2$iPr.

Leaving groups which can be represented by X$^1$ and X$^2$ include chloro, bromo and iodo, especially chloro, groups, and alkoxy groups, especially C$_{1-4}$alkoxy, such as methoxy, groups. Commonly when X$^1$ and X$^2$ are leaving groups, either both are selected from chloro, bromo or iodo, or both are alkoxy. It is most preferred that X$^1$ and X$^2$ together represent =O.

Oxidising agents which may be employed in the process according to the present invention include those oxidising agents known in the art to oxidise dihydropyrimidines to pyrimidines. Examples of suitable oxidising agents include quinones, such as chloranil, and particularly substituted benzoquinones such as 2,3-dichloro-5,6-dicyano-1,4-benzoquinone; halogens, such as bromine, transition metal oxidants such as barium manganate, copper chloride, optionally in the presence of phenanthroline, and manganese dioxide; metallic oxidants, such as palladium on charcoal or other suitable platinum group metals; and elemental sulfur. The most preferred oxidants are elemental sulfur and manganese dioxide.

In certain embodiments of the present invention, particularly when E represents H or unsubstituted alkyl, and especially H, the product of the reaction obtained from step (a) is the substituted pyrimidine rather than a dihydropyrimidine. Without wishing to be bound by any theory, it is believed that any dihydropyrimidine formed is autoxidised to the pyrimidine by the presence of oxygen, or the dihydropyrimidine self-oxidises or disproportionates.

Preferred compounds of formula R$^1$—CO—CH$_2$-E are compounds of formula (C$_{1-4}$alkyl)-CO—CH$_2$CO$_2$R$^5$, wherein R$^5$ represents a C$_{1-4}$ alkyl group, especially a methyl, ethyl or isopropyl group. Most preferred compounds of formula R$^1$—CO—CH$_2$-E are compounds of formulae:

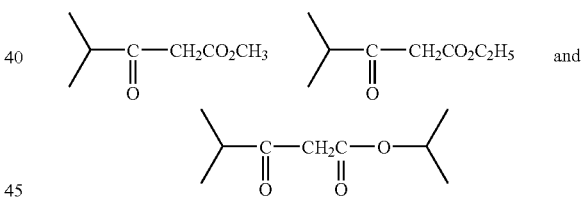

Compounds of formula (CH$_3$)$_2$CH—CO—CH$_2$—CO$_2$—C$_3$H$_7$, preferably (CH$_3$)$_2$CH—CO—CH$_2$—CO$_2$—CH(CH$_3$)$_2$, form another aspect of the present invention. Such compounds may be prepared by methods analogous to those known in the art for the preparation of similar compounds, such as methyl isobutyrylacetate and ethyl isobutyrylacetate.

Preferred compounds of formula R$^2$—CHX$^1$X$^2$ are compounds of formula:

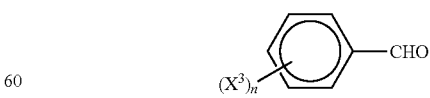

wherein X$^3$ represents a substituent, especially halo, and n is 0 or 1-5. Preferably X$^3$ is chloro or fluoro, alkyl, preferably methyl, or alkoxy, preferably methoxy. Most preferably n is 1, and X$^3$ is present at the 4-position. Especially preferred is 4-fluorobenzaldehyde.

Preferred compounds of formula $R^3R^4N$—$C(=NH)NH_2$ are guanidine and methylguanidine. The compounds of formula $R^3R^4N$—$C(=NH)NH_2$ can be employed as the free base, but in many embodiments are advantageously employed as a salt, such as a nitrate, carbonate or sulphate salt, and especially a hydrochloride salt.

Preferred catalysts which can be employed in the present invention are bases.

Bases which can be employed in the process of the present invention are preferably inorganic bases. Examples of inorganic bases include alkali and alkaline earth metal carbonates and hydrogencarbonates, particularly sodium or potassium hydrogencarbonate and most preferably sodium or potassium carbonate.

Step a) of the process according to the present invention preferably employs a solvent which is inert under the reaction conditions employed. In many embodiments, a polar solvent is employed, preferably a polar aprotic solvent, for example including dichloromethane, dimethylsulphoxide and tetrahydrofuran. Preferred solvents are amides, such as N-methylpyrrolidinone and especially dimethylformamide and dimethylacetamide. Mixtures of solvents may be employed if desired.

In many preferred embodiments of the present invention, a mixture comprising the compound of formula $R^1$—CO—$CH_2$-E, compound of formula $R^2$—$CHX^1X^2$ and compound of formula $R^3R^4N$—$C(=NH)NH_2$ is formed, optionally in the presence of a solvent, and the catalyst added to this mixture.

It will be recognised that the reaction conditions employed in Step a) of the present invention the process may be varied over a wide range, depending for example on the nature of the reagents and/or solvent employed. Step a) commonly employs a reaction temperature in the range of from about 50° C. to about 80° C., such as from about 55° to 65° C. In many embodiments, a mole ratio of compound of formula $R^3R^4N$—$C(=NH)NH_2$ to compound of formula $R^1$—CO—$CH_2$-E of from about 1.5:1 to about 3.5:1, such as about 2:1, can be advantageously employed. In many embodiments, a stoichiometric mole ratio, or a small molar excess, such as up to about 1.2:1, of compound of formula $R^2$—$CHX^1X^2$ to compound of formula $R^1$—CO—$CH_2$-E is employed.

Step b) of the process preferably employs a solvent which is inert under the reaction conditions employed. The solvent is selected according to the nature of the oxidising agent employed, and may include the solvents described above for step a). Further solvents which may be employed in step b) include non-polar solvents, for example hydrocarbons, such as toluene, and dialkylethers, such as methyl tertiary-butyl ether. Mixtures of solvents may be employed if desired.

It will be recognised that the reaction conditions employed in Step b) of the process according to the present invention may be varied over a wide range, depending for example on the nature of the oxidant and/or solvent employed. Step b) commonly employs a reaction temperature in the range of from about 50° C. to about 140° C., such as from about 100° C. to 120° C. In many embodiments, a stoichiometric mole ratio, or a molar excess of oxidant to dihydropyrimidine is employed. In certain highly preferred embodiments, the oxidant employed is $MnO_2$ and azeotropic conditions are employed, most preferably employing toluene as solvent, with a mole ratio of $MnO_2$ to dihydropyrimidine of from about 2:1 to 4:1 being especially preferred.

Compounds of Formula (2) and tautomers thereof, especially compounds of Formula (2a), wherein E is not H, $R^3$ and $R^4$ are not both unsubstituted alkyl groups and $R^1$ is not —$CH_3$ when $R^2$ is unsubstituted phenyl or o-nitrophenyl are novel, and accordingly form a second aspect of the present invention. In such compounds, it is preferred that at least one of $R^3$ and $R^4$ represents H, and that $R^2$ preferably represents a phenyl group substituted by one or more halogens, and most preferably represents a 4-fluorophenyl group.

Step a) of the process according to the first aspect of present invention forms a third aspect of the present invention.

Step b) of the process according to the first aspect of present invention forms a fourth aspect of the present invention.

When either or both of $R^3$ and $R^4$ is H, the compounds of Formulae (1) or (2) may be reacted with reagents to introduce a substituent onto the exocyclic nitrogen, especially to introduce an alkyl, especially a methyl, or an alkyl- or arylsulfonyl, especially a mesyl, substituent.

In a particularly preferred aspect of the present invention, there is provided a process for the preparation of a compound of Formula (3):

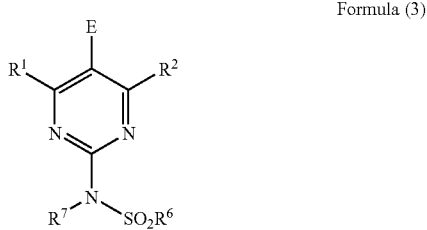

Formula (3)

which comprises a) reacting a compound of formula $R^1$—CO—$CH_2$-E with a compound of formula $R^2$—$CHX^1X^2$ in the presence of a compound of formula $R^7HN$—$C(=NH)NH_2$ and a catalyst, thereby to form a dihydropyrimidine, which may be represented by a compound of formula (2) or (2a) as described above but in which $R^3$ represents $R^7$ and $R^4$ is H;

b) oxidising the dihydropyrimidine produced in step a) to form a compound of Formula (4)

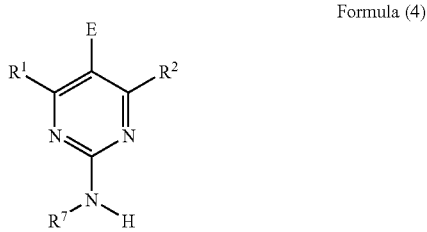

Formula (4)

and c) reacting the compound of Formula (4) with a compound of formula $R^6SO_2$—$X^4$ to give a compound of Formula (3);

wherein $R^1$, $R^2$; E, $X^1$ and $X^2$ are as previously described;

$R^6$ represents alky or aryl, preferably methyl;

$R^7$ is H, alkyl or aryl; and $X^4$ represents a leaving group, preferably Cl or Br.

Alkyl and aryl groups which may be represented by $R^7$ are as described above for $R^3$. In many embodiments, $R^7$ represents H or a methyl group.

Preferred features for $R^1$, $R^2$; E, $X^1$ and $X^2$ are as previously described.

The present invention is illustrated further, without limitation, by the following examples.

EXAMPLE 1

Preparation of Methyl 2-amino-4-(4-fluorophenyl)-6-isopropyl-pyrimidine-5-carboxylate a) A 100 ml two neck round bottom flask equipped with a condenser and connected to a nitrogen line was charged with p-fluorobenzaldehyde (0.57 ml, 5 mmol), methyl isobutyrylacetate ("MIBA", 0.79 g, 5.5 mmol), guanidine hydrochloride (1.19 g, 12.5 mmol), potassium carbonate (2.76 g, 40 mmol) and 10 ml of anhydrous dimethylformamide (DMF). This mixture was stirred and heated at 70° C. for 20 h. The reaction mixture changed from colourless to yellow during this time. After cooling, DMF was removed under vacuum and the residue partitioned between brine (50 ml) and ethyl acetate (200 ml). The aqueous phase was washed with ethyl acetate (200 ml) and the combined organic layers were dried over magnesium sulfate and filtered. The solvent was removed under vacuum to obtain 1 g of yellow solid. $^1$HNMR and LC showed methyl 2-amino-4-(4-fluorophenyl)-6-isopropyl-1,6-dihydropyrimidine-5-carboxylate as the major component (82%).

$^1$H NMR (250 MHz, $C_2D_6SO$); δ 0.95-1.1 (2×d, 6H, $CH(CH_3)_2$), 3.45 (s, 3H, O—$CH_3$), 4.0 (septet, 1H, $CH(CH_3)_2$), 6.1 (broad s, 2H, $NH_2$), 7.1-7.3 (m, 5-H, N—H & 4C—H aromatic).

b) A 25 ml three neck round bottom flask evacuated and back-filled with nitrogen was charged with methyl 2-amino-4-(4-fluorophenyl)-6-isopropyl-1,6-dihydropyrimidine-5-carboxylate (100 mg) and 15 ml of anhydrous THF. 2,3-Dichloro-5,6-dicyano-1,4-benzoquinone (135 mg, 0.45 mmol) was added under nitrogen. The red solution was stirred at room temperature. After 40 min, methyl 2-amino-4-(4-fluorophenyl)-6-isopropyl-pyrimidine-5-carboxylate was observed by HPLC and LC-MS. The product was identified by comparison with a standard of high purity prepared by a different chemical route. Both samples co-eluted by HPLC and showed the same ions by positive and negative electrospray mass spectrometry.

EXAMPLE 2

Preparation of Methyl 2-amino-4-(4-fluorophenyl)-6-isopropyl-1,6-dihydropyrimidine-5-carboxylate Guanidine hydrochloride (12.1 g), 4-Fluorobenzaldehyde (7.0 g), methyl 4-methyl-3-oxo-pentanoate (8.9 g) and DMF (150 ml) were charged to a vessel equipped with a condenser and connected to a nitrogen line. The resultant mixture was stirred until a clear solution was obtained. Potassium carbonate (17.5 g) is charged and the mixture heated to 70° C. for 3 hours. The reaction mixture was cooled to ambient temperature and filtered. It contained methyl 2-amino-4-(4-fluorophenyl)-6-isopropyl-1,6-dihydropyrimidine-5-carboxylate in 55% yield. An analytical sample was prepared by removing the reaction solvents by evaporation under reduced pressure, precipitating the product from the resultant oil in acetonitrile and recrystallisation from acetonitrile.

$^1$H NMR (250 MHz, $C_2D_6SO$); δ 0.95-1.1 (2×d, 6H, $CH(CH_3)_2$), 3.45 (s, 3H, O—$CH_3$), 4.0 (septet, 1H, $CH(CH_3)_2$), 6.1 (broad s, 2H, $NH_2$), 7.1-7.3 (m, 5-H, N—H & 4C—H aromatic).

EXAMPLE 3

Preparation of Ethyl 2-amino-4-(4-fluorophenyl)-6-isopropyl-1,6-dihydropyrimidine-5-carboxylate Guanidine hydrochloride (24.1 g), 4-Fluorobenzaldehyde (13.9 g), ethyl 4-methyl-3-oxo-pentanoate (16.2 g) and DMF (300 ml) were charged to a vessel equipped with a condenser and connected to a nitrogen line. The resultant mixture was stirred until a clear solution was obtained. Sodium carbonate (26.8 g) was charged and the mixture heated to 70° C. for 4 hours. The reaction mixture contained ethyl 2-amino-4-(4-fluorophenyl)-6-isopropyl-1,6-dihydropyrimidine-5-carboxylate in 75% yield. DMF was removed by evaporation under reduced pressure until the reaction mixture contained 35-40% DMF by weight. Toluene was charged (112 ml) and the temperature adjusted to 55° C. This solution was washed 3 times with 10% aqueous sodium chloride solution, cooled to 10° C., washed with toluene (32 ml) and dried in a vacuum oven at 50° C.

$^1$H NMR (250 MHz, $C_2D_6SO$); δ 1.0 (t, 3H, $CH_2CH_3$), 1.1 (d, 6H, $CH(CH_3)_2$), 3.9 (q, 2H, $CH_2CH_3$), 4.05 (septet, 1H, $CH(CH_3)_2$), 5.2 (s, 1H, N—C—H), 6.1 (broad s, 2H, $NH_2$), 7.1 (t, 2H, C—H aromatic), 7.15-7.3 (m, 3H, N—H & 2C—H aromatic).

EXAMPLE 4

Preparation of Isopropyl 4-methyl-3-oxo-pentanoate

Methyl 4-methyl-3-oxo-pentanoate (304 g), isopropyl alcohol (500 ml) and p-toluenesulfonic acid (3.8 g) were stirred together and heated to reflux at 90° C. After 3 hours, 400 ml of solvent was collected by distillation at atmospheric pressure. Fresh isopropyl alcohol was added and the mixture refluxed for a further 3 hours. The cycle of distillation, addition of fresh solvent and refluxing was continued until the conversion had reached 95%, determined by a peak area ratio of product:starting material of 95:5 measured by LC. The remaining volatile solvents were removed by distillation and the resultant liquid washed with 10% sodium carbonate solution and dried over anhydrous sodium sulfate and filtered to give isopropyl 4-methyl-3-oxo-pentanoate as a clear liquid (301 g, 83%).

$^1$H NMR (250 MHz, $C_2D_6SO$); δ 1.05, 1.2 (2×d, 12H, C—$CH(CH_3)_2$, O—$CH(CH_3)_2$), 2.7 (septet, 1H, C—$CH(CH_3)_2$), 3.6 (s, 2H, $CH_2$), 4.05 (septet, 1H, O—$CH(CH_3)_2$)

EXAMPLE 5

Preparation of Isopropyl 2-amino-4-(4-fluorophenyl)-6-isopropyl-1,6-dihydropyrimidine-5-carboxylate Guanidine hydrochloride (12.1 g), 4-Fluorobenzaldehyde (7.0 g), isopropyl 4-methyl-3-oxo-pentanoate (8.9 g) and DMF (150 ml) were charged to a vessel equipped with a condenser and connected to a nitrogen line. The resultant mixture was stirred until a clear solution was obtained. Potassium carbonate (17.5 g) was charged and the mixture heated to 70° C. for 3 hours. The reaction mixture was cooled to ambient temperature, filtered, and the solvents removed by evaporation under reduced pressure. The resultant oil was triturated in water at 80° C. and cooled to give a slurry that was filtered and dried to give isopropyl 2-amino-4-(4-fluorophenyl)-6-isopropyl-1,6-dihydropyrimidine-5-carboxylate in 67% yield.

$^1$H NMR (250 MHz, C$_2$D$_6$SO); δ 0.9-1.15 (d, 12H, C—CH(CH$_3$)$_2$, O—CH(CH$_3$)$_2$), 4.0 (septet, 1H, C—CH(CH$_3$)$_2$), 4.75 (septet, 1H, O—CH(CH$_3$)$_2$), 5.2 (s, 1H, N—C—H), 6.1 (broad s, 2H, NH$_2$), 7.1 (t, 2H, C—H aromatic), 7.2 (m, 3H, N—H & 2C—H aromatic).

EXAMPLE 6

Preparation of Ethyl 4-(4-fluorophenyl)-6-isopropyl-2-methylamino-1,6-dihydropyrimidine-5-carboxylate 1-Methylguanidine hydrochloride (8.25 g), 4-Fluorobenzaldehyde (4.2 g), ethyl 4-methyl-3-oxo-pentanoate (5.0 g) and DMF (100 ml) were charged to a vessel equipped with a condenser and connected to a nitrogen line. The resultant mixture stirred until a clear solution is obtained. Sodium carbonate (4.0 g) was charged and the mixture heated to 70° C. for 2 hours. The reaction mixture was cooled to ambient temperature, filtered, and the solvents removed by evaporation under reduced pressure. The resultant oil was triturated in water at 50° C. and cooled to give a slurry that was filtered and dried to give ethyl 4-(4-fluorophenyl)-6-isopropyl-2-methylamino-1,6-dihydropyrimidine-5-carboxylate in 63% yield.

$^1$H NMR (250 MHz, C$_2$D$_6$SO); δ 0.95-1.1 (m, 9H, CH$_2$CH$_3$ & CH(CH$_3$)$_2$), 2.7 (s, 3H, NH—CH$_3$), 3.9 (q, 2H, CH$_2$CH$_3$), 4.0 (septet, 1H, CH(CH$_3$)$_2$), 5.2 (s, 1H, N—C—H), 6.4 (broad s, 1H, NH—CH$_3$), 7.1 (t, 2H, C—H aromatic), 7.2 (m, 3H, N—H & 2C—H aromatic).

EXAMPLE 7

Preparation of Methyl 4-(4-fluorophenyl)-6-isopropyl-2-(1-pyrazolyl)-1,6-dihydropyrimidine-5-carboxylate 1H-Pyrazole carboxamidine (prepared according to the method of Bernatowicz, Wu and Matsueda; *J. Org. Chem.*, 52, 2497-2502, 1992; 0.91 g), 4-Fluorobenzaldehyde (0.37 g), methyl 4-methyl-3-oxo-pentanoate (0.4 g), potassium carbonate (1.38 g) and DMF (10 ml) were charged to a small vessel. The resultant mixture was heated to 85° C. for 6 hours. The reaction mixture was cooled to ambient temperature, filtered, and the solvents removed by evaporation under reduced pressure. The resultant oil was triturated in water to give a slurry that was filtered, washed and dried. The major component isolated by column chromatography was Methyl 4-(4-fluorophenyl)-6-isopropyl-2-(1-pyrazolyl)-1,6-dihydropyrimidine-5-carboxylate.

$^1$H NMR (250 MHz, C$_2$D$_6$SO); δ 1.05-1.2 (2×d, 6H, CH(CH$_3$)$_2$), 3.55 (s, 3H, O—CH$_3$), 4.0 (septet, 1H, CH(CH$_3$)$_2$), 5.5 (s, 1H, N—C—H), 6.55 (m, 1H, pyrazolyl C—H), 7.0 (t, 2H, phenyl C—H), 7.3 (m, 3H, N—H & 2 phenyl C—H), 7.7 (m, 1H, pyrazolyl C—H), 8.4 (m, 1H, pyrazolyl C—H).

EXAMPLE 8

Preparation of 2-amino-4-(4-fluorophenyl)-6-isopropyl-pyrimidine

Guanidine hydrochloride (1.19 g), 4-Fluorobenzaldehyde (0.62 g), 3-methyl butan-2-one (0.47 g) and DMF (20 ml) were charged to a flask. The resultant mixture was stirred until a clear solution was obtained. Sodium tert-butoxide (2.36 g) was charged and the mixture stirred at ambient temperature for 18 hours. The reaction mixture contained 2-amino-4-(4-fluorophenyl)-6-isopropyl-pyrimidine in 30% yield. The major component was isolated by flash column chromatography on silica, eluting with ethyl acetate/hexanes (1:4).

$^1$H NMR (250 MHz, CDCl$_3$); δ 1.25 (d, 6H, CH(CH$_3$)$_2$), 2.8 (septet, 1H, CH(CH$_3$)$_2$), 6.6 (broad s, 2H, NH$_2$), 7.35 (t, 2H, C—H aromatic), 8.15 (m, 2C—H aromatic).

EXAMPLE 9

Preparation of Ethyl 2-amino-4-(4-fluorophenyl)-6-isopropyl-pyrimidine-5-carboxylate Ethyl 2-amino-4-(4-fluorophenyl)-6-isopropyl-1,6-dihydropyrimidine-5-carboxylate (22.6 g) was dissolved in toluene (150 ml) and heated until a solution was obtained. Manganese dioxide (18.8 g) was added as a slurry in toluene (150 ml) and the mixture refluxed under azeotropic conditions for 6 hours until conversion was complete. A small amount of water was collected in the Dean and Stark trap. The slurry was filtered and the solvents removed by evaporation under reduced pressure to give ethyl 2-amino-4-(4-fluorophenyl)-6-isopropyl-pyrimidine-5-carboxylate as a crystalline solid in 96% yield.

$^1$H NMR (250 MHz, C$_2$D$_6$SO); δ 0.95 (t, 3H, CH$_2$CH$_3$), 1.2 (d, 6H, CH(CH$_3$)$_2$), 3.1 (septet, 1H, CH(CH$_3$)$_2$), 4.05 (q, 2H, CH$_2$CH$_3$), 7.1 (broad s, 2H, NH$_2$), 7.3 (t, 2H, C—H aromatic), 7.55 (m, 2C—H aromatic).

EXAMPLE 10

Preparation of Ethyl 2-amino-4-(4-fluorophenyl)-6-isopropyl-pyrimidine-5-carboxylate The process of Example 9 was repeated, but using elemental sulfur (4.7 g) in place of the manganese dioxide, and a reaction time of 24 hours. The product was obtained in a near quantitative conversion.

EXAMPLE 11

Preparation of Ethyl 4-(4-fluorophenyl)-6-isopropyl-2-methylamino-pyrimidine-5-carboxylate The process of Example 9 was repeated but employing 10 mmol of ethyl 4-(4-fluorophenyl)-6-isopropyl-2-methylamino-1,6-dihydropyrimidine-5-carboxylate in place of ethyl 2-amino-4-(4-fluorophenyl)-6-isopropyl-1,6-dihydropyrimidine-5-carboxylate, with the other reagents and components reduced proportionately. The product was obtained in a near quantitative conversion.

$^1$H NMR (250 MHz, C$_2$D$_6$SO); δ 0.95 (t, 3H, CH$_2$CH$_3$), 1.2 (d, 6H, CH(CH$_3$)$_2$), 2.85 (d, 3H, N—CH$_3$), 3.1 (septet, 1H, CH(CH$_3$)$_2$), 4.05 (q, 2H, CH$_2$CH$_3$), 7.3 (t, 2H, C—H aromatic), 7.45-7.65 (broad s, 3-H, N—H & 2C—H aromatic).

The invention claimed is:

1. A compound of Formula (2a), and tautomers thereof:

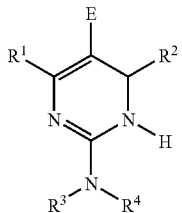

Formula (2a)

wherein $R^1$ is H or an alkyl group;

$R^2$ is H, an alkyl or aryl group;

$R^3$ and $R^4$ are each independently H, alkyl, or aryl, provided that $R^3$ and $R^4$ are not both unsubstituted alkyl; and E represents a group of formula $CO_2(C_{1-4}alkyl)$, further provided that $R^1$ is not $-CH_3$ when $R^2$ is unsubstituted phenyl or o-nitrophenyl, and wherein optional substituents for alkyl, aryl or heteroaryl groups $R^1$, $R^2$, $R^3$ or $R^4$ are selected from optionally substituted $C_{1-4}$-alkyl, optionally substituted aryl, optionally substituted aryloxy, optionally substituted heterocyclyl, polyalkylene oxide, carboxy, oxo, phosphato, sulpho, nitro, cyano, halo, ureido, $-SO_2F$, ester, $NR^aR^b$, $COR^a$, $CONR^aR^b$, $-NHCOR^a$, carboxyester, sulphone, and $-SO_2NR^aR^b$ wherein $R^a$ and $R^b$ are each independently H, optionally substituted alkyl $C_{1-4}$-alkyl) or optionally substituted aryl, or, in the case of $NR^aR^b$, $-CONR^aR^b$ and $-SO_2R^aR^b$, $R^a$ and $R^b$ together with the nitrogen atom to which they are attached may represent an aliphatic or aromatic ring system and wherein optional substituents for any of the substituents described may be selected from $C_{1-4}$-alkoxy, $C_{1-4}$-alkyl, aryl, aryloxy, heterocyclyl, polyalkylene oxide, carboxy, oxo, phosphato, sulpho, nitro, cyano, halo, ureido, $-SO_2F$, hydroxy, ester, $NR^aR^b$, $COR^a$, $CONR^aR^b$, $-NHCOR^a$, carboxyester, sulphone, and $-SO_2NR^aR^b$ wherein $R^a$ and $R^b$ are each independently H, $C_{1-4}$-alkyl or aryl, or, in the case of $NR^aR^b$, $-CONR^aR^b$ and $-SO_2NR^aR^b$, $R^a$ and $R^b$ together with the nitrogen atom to which they are attached may represent an aliphatic or aromatic ring system.

2. The compound according to claim 1, wherein $R^2$ is a phenyl group substituted by one or more halogens.

3. The compound according to claim 1, wherein at least one of $R^3$ and $R^4$ is H.

4. The compound according to claim 1, wherein $R^1$ is isopropyl and $R^2$ is 4-fluorophenyl.

5. The compound according to claim 1, wherein $R^3$ is H or methyl and $R^4$ is H.

6. A process for preparing a compound of Formula (2a) and tautomers thereof:

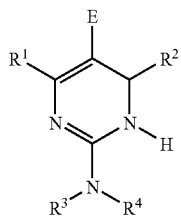

Formula (2a)

which comprises a) reacting a compound of formula $R^1-CO-CH2-E$ with a compound of formula $R^2-CHX^1X^2$ in the presence of a compound of formula $R^3R^4N-C(=NH)NH_2$ and a catalyst, thereby forming the compound of Formula (2a), wherein $R^1$ is an H or an alkyl group;

$R^2$ is an H or an alkyl or aryl group;

$R^3$ and $R^4$ are each independently H, alkyl or aryl, or $R^3$ and $R^4$ are linked to form, together with the nitrogen to which they are attached, a 5- to 7-membered heterocyclic ring, wherein optional substitutents for alkyl, aryl or heteroaryl groups $R^1$, $R^2$, $R^3$ or $R^4$ are selected from optionally substituted $C_{1-4}$-alkyl, optionally substituted aryl, optionally substituted aryloxy, optionally substituted heterocyclyl, polyalkylene oxide, carboxy, oxo phosphato, sulpho, nitro, cyano, halo, ureido, $-SO_2F$, ester, $-NR^aR^b$, $-COR^a$, $-CONR^aR^b$, $-NHCOR^a$, carboxyester, sulphone, and $-SO_2NR^aR^b$ wherein $R^a$ and $R^b$ are each independently H, optionally substituted alkyl $C_{1-4}$-alkyl) or optionally substituted aryl, or, in the case of $-NR^aR^b$, $CONR^aR^b$ and $-SO_2NR^aR^b$, $R^a$ and $R^b$ together with the nitrogen atom to which they are attached may represent an aliphatic or aromatic ring system and wherein optional substituents for any of the substituents described may be selected from $C_{1-4}$-alkoxy, $C_{1-4}$-alkyl, aryl, aryloxy, heterocyclyl, polyalkylene oxide, carboxy, oxo, phosphato, sulpho, nitro, cyano, halo, ureido, $-SO_2F$, hydroxy, ester, $-NR^aR^b$, $-COR^a$, $-CONR^aR^b$, $-NHCOR^a$, carboxyester, sulphone, and $-SO_2NR^aR^b$ wherein $R^a$ and $R^b$ are each independently H, $C_{1-4}$-alkyl or aryl, or, in the case of $-NR^aR^b$, $-CONR^aR^b$ and $-SO_2NR^aR^b$, $R^a$ and $R^b$ together with the nitrogen atom to which they are attached may represent an aliphatic or aromatic ring system;

E is a group of formula $-CO_2(C_{1-4}alkyl)$; and $X^1$ and $X^2$ are each independently leaving groups, or $X^1$ and $X^2$ together are $=O$.

7. The process according to claim 6, wherein $R^1$ is isopropyl, $R^2$ is $R^4$-fluorophenyl, and $R^3$ and $R^4$ are each independently H or methyl.

8. The process according to claim 7, wherein $R^3$ is methyl and $R^4$ is H.

* * * * *